US011229756B2

(12) United States Patent
Silver et al.

(10) Patent No.: US 11,229,756 B2
(45) Date of Patent: Jan. 25, 2022

(54) MULTIMODAL SURGICAL GAS DELIVERY SYSTEM CONFIGURED TO MAINTAIN STABLE BODY CAVITY PRESSURE WHEN SUCTION IS USED IN THE BODY CAVITY

(71) Applicant: Conmed Corporation, Utica, NY (US)

(72) Inventors: Mikiya Silver, New Haven, CT (US); George R. Trutza, East Greenwich, RI (US); Michael J. Kane, Clinton, CT (US)

(73) Assignee: Conmed Corporation, Utica, NY (US)

( * ) Notice: Subject to any disclaimer, the term of this patent is extended or adjusted under 35 U.S.C. 154(b) by 350 days.

(21) Appl. No.: 15/812,724

(22) Filed: Nov. 14, 2017

(65) Prior Publication Data

US 2018/0133416 A1    May 17, 2018

Related U.S. Application Data

(60) Provisional application No. 62/421,543, filed on Nov. 14, 2016.

(51) Int. Cl.
*A61M 13/00* (2006.01)
*A61M 3/02* (2006.01)
(Continued)

(52) U.S. Cl.
CPC ....... *A61M 13/003* (2013.01); *A61B 17/3474* (2013.01); *A61B 18/14* (2013.01);
(Continued)

(58) Field of Classification Search
CPC ............ A61B 17/3474; A61B 17/0218; A61B 17/3421; A61B 2218/007;
(Continued)

(56) References Cited

U.S. PATENT DOCUMENTS 5,139,478 A    8/1992 Koninckx et al.
5,246,419 A    9/1993 Absten
(Continued)

FOREIGN PATENT DOCUMENTS

JP    H06178780 A    6/1994
JP    2006-288754 A    10/2006
(Continued)

OTHER PUBLICATIONS

International Search Report and Written Opinion, issued in corresponding PCT Patent Application No. PCT/US2017/061483, dated Mar. 2, 2018.
(Continued)

*Primary Examiner* — Lauren P Farrar
*Assistant Examiner* — Hamza A Darb
(74) *Attorney, Agent, or Firm* — Locke Lord LLP; Scott D. Wofsy

(57) ABSTRACT

A system is disclosed for delivering insufflation gas to a body cavity of a patient during a surgical procedure, which includes an insufflator for delivering a flow of insufflation gas to the body cavity of the patient through a flow path that communicates with a pneumatically sealed trocar, a flow meter for measuring an amount of gas that has been removed from the body cavity by use of a suction device, and a controller operatively connected to the flow meter for receiving a flow measurement from the flow meter to determine when the suction device is in use and an amount of insufflation gas needed to be delivered to the body cavity by the insufflator to compensate for the gas removed from the body cavity by the suction device.

11 Claims, 5 Drawing Sheets

(51) Int. Cl.
*A61B 17/34* (2006.01)
*A61B 18/00* (2006.01)
*A61M 1/00* (2006.01)
*A61B 18/14* (2006.01)

(52) U.S. Cl.
CPC ............ *A61M 1/84* (2021.05); *A61M 3/0283* (2013.01); *A61M 13/006* (2014.02); *A61B 17/3478* (2013.01); *A61B 2018/00595* (2013.01); *A61B 2218/007* (2013.01); *A61B 2218/008* (2013.01); *A61M 2205/3334* (2013.01); *A61M 2205/3337* (2013.01); *A61M 2205/3344* (2013.01); *A61M 2205/3569* (2013.01); *A61M 2205/3576* (2013.01); *A61M 2205/3584* (2013.01); *A61M 2205/3592* (2013.01); *A61M 2205/50* (2013.01); *A61M 2205/502* (2013.01); *A61M 2205/75* (2013.01); *A61M 2210/1021* (2013.01)

(58) Field of Classification Search
CPC .............. A61B 2218/008; A61B 18/14; A61B 17/3478; A61B 2018/00595; A61M 2205/3344; A61M 13/003; A61M 1/0029; A61M 1/0025; A61M 13/006; A61M 1/008; A61M 2205/3592; A61M 2205/3569; A61M 2210/1021; A61M 1/0031; A61M 2205/3584; A61M 2205/3576; A61M 2205/3337; A61M 2205/3334; A61M 1/006; A61M 1/84; A61M 1/734; A61M 1/777; A61M 1/74; A61M 2205/33; A61M 2205/50; A61M 2205/502; A61M 2205/75; A61M 3/0283
See application file for complete search history.

(56) References Cited

U.S. PATENT DOCUMENTS

| | | | |
|---|---|---|---|
| 7,255,693 B1* | 8/2007 | Johnston | A61B 18/02 606/20 |
| 7,335,159 B2* | 2/2008 | Banik | A61B 1/00094 600/129 |
| 2005/0137529 A1 | 6/2005 | Mantell | |
| 2005/0217727 A1* | 10/2005 | Uesugi | A61M 13/003 137/315.01 |
| 2007/0088275 A1* | 4/2007 | Stearns | A61M 1/28 604/164.01 |
| 2007/0249990 A1 | 10/2007 | Cosmescu | |
| 2012/0184897 A1* | 7/2012 | Poll | A61B 1/015 604/24 |
| 2017/0000959 A1* | 1/2017 | Mantell | A61B 17/3474 |

FOREIGN PATENT DOCUMENTS

| | | |
|---|---|---|
| JP | 2014-113256 A | 6/2014 |
| JP | 5509178 B2 | 6/2014 |

OTHER PUBLICATIONS

English translation of Office Action issued in corresponding Japanese Patent Application No. JP 2019-524883, dated Nov. 4, 2020.
Office Action issued in corresponding Korean Patent Application No. KR-10-2019-7016584, dated Dec. 22, 2020.

* cited by examiner

MULTIMODAL SURGICAL GAS DELIVERY SYSTEM CONFIGURED TO MAINTAIN STABLE BODY CAVITY PRESSURE WHEN SUCTION IS USED IN THE BODY CAVITY

CROSS-REFERENCE TO RELATED APPLICATION

The subject application claims the benefit of priority to U.S. Provisional Patent Application Ser. No. 62/421,543 filed Nov. 14, 2016, the disclosure of which is herein incorporated by reference in its entirety.

BACKGROUND OF THE INVENTION

1. Field of the Invention

The subject invention relates to surgical gas delivery systems, and more particularly, to multimodal gas delivery systems for surgical insufflation, smoke evacuation and/or gas recirculation, which is also configured to maintain body cavity pressure when suction is used in the body cavity during a surgical procedure.

2. Background of the Related Art

Minimally invasive surgical techniques such as endoscopic and laparoscopic surgical procedures have become increasingly common. Benefits of such procedures include reduced trauma to the patient, reduced opportunity for infection and decreased recovery time. Laparoscopic surgical procedures within the abdominal (peritoneal) cavity are typically performed through a device known as a trocar or cannula, which facilitates the introduction of surgical instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by way of a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, often using a separate inserter or obturator placed therein. Following insertion, the inserter is removed, and the trocar allows access for instruments to be inserted into the abdominal cavity. Typical trocars provide a way to insufflate the abdominal cavity, so that the surgeon has an open interior space in which to operate and work.

The trocar must maintain the pressure within the abdominal cavity by providing a seal between the trocar and any surgical instrument being passed therethrough, while still allowing at least a minimum freedom of movement of the surgical instruments. Such instruments can include, for example, scissors, grasping instruments, and occluding instruments, cauterizing units, cameras, light sources and other surgical instruments.

Sealing elements or mechanisms are typically provided within trocars to prevent the escape of insufflation gas. These typically include a duckbill-type valve made of a relatively pliable material, to seal around an outer surface of surgical instruments passing through the trocar.

Surgical access devices or trocars that permit sealed access to an insufflated surgical cavity without the need for conventional mechanical seals are known in the art. These devices are adapted and configured to provide sealable access to a surgical cavity through the use of a pneumatic or gaseous seal generated and maintained by a circulating flow of pressurized insufflation gas. Such devices are described in U.S. Pat. Nos. 7,854,724 and 8,795,223, the disclosures of which are herein incorporated by reference in their entireties. Also known in the art are multimodal surgical gas delivery systems that are used in conjunction with such pneumatically sealed trocars for delivering insufflation gas to a body cavity, for circulating surgical gas through the trocar to generate and maintain the pneumatic seal and for facilitating smoke evacuation from the body cavity.

Use of a multimodal system helps to reduce costs by requiring purchase of only one system, while achieving multiple functions, and also thereby reduces the amount of equipment needed in an operating room, thus reducing clutter and allowing space for other necessary equipment. Such systems are described for example in U.S. Pat. Nos. 8,715,219 and 8,961,451 as well as in U.S. Pat. Nos. 9,295,490 and 9,375,539, the disclosures of which are all herein incorporated by reference in their entireties.

It is also known to perform electrocautery and other surgical techniques (e.g. harmonic scalpels) during laparoscopic surgery. These techniques produce smoke and other debris in the surgical cavity. This can reduce visibility by fogging the view from endoscopes and the like. Occasionally, suction is introduced at the surgical cavity to remove debris, smoke, bodily fluids, or irrigation liquid during a surgical procedure. Actuation of the suction mechanism changes the pressure at the surgical cavity by pulling a vacuum on the insufflation gas used to form the pneumoperitoneum.

The removal of the insufflation gas can cause a reduction in the working space at the surgical cavity. Often the suction mechanism removes gas at a higher rate than a conventional insufflator is able to replenish the gas levels in the cavity. Consequently, the pneumoperitoneum at the surgical cavity will become unstable as the suction mechanism and the insufflator work in opposition to each other. This can create visualization issues for the surgeon.

It would be advantageous for the insufflator to act in concert with the suction mechanism or device so as to maintain the stability of the pneumoperitoneum within the surgical cavity, instead of reacting or overreacting to the loss of pressure resulting from actuation of the suction mechanism. The subject invention provides a system for this purpose.

While such a system would be advantageous in the performance of laparoscopic surgical procedures within the abdominal cavity of a patient, it is envisioned and well within the scope of the subject disclosure that such a system can be utilized in thoracic, colorectal, uterine and other endoscopic procedures.

SUMMARY OF THE INVENTION

The subject invention is directed to new and useful systems for delivering insufflation gas to a body cavity of a patient during a surgical procedure. In one embodiment of the subject invention, the system includes an insufflator for delivering insufflation gas to the body cavity of a patient through a flow path, a suction device connected to a vacuum source for removing solid, liquids and gases from the body cavity during the surgical procedure, and a conduit providing communication between the vacuum source and the suction device.

The system further includes a flow meter communicating with the conduit for measuring an amount of gas flowing through the conduit that has been removed from the body cavity by use of the suction device, and a controller that is operatively connected to the flow meter for receiving a flow measurement from the flow meter to determine when the suction device is in use (i.e., started and/or stopped) and an amount of insufflation gas needed to be delivered to the body cavity by the insufflator to compensate for the gas removed from the body cavity by the suction device.

In one aspect of the invention, the controller is adapted and configured to cause the insufflator to increase the flow of insufflation gas through the flow path to compensate for the gas removed from the body cavity by the suction device. In another aspect of the invention, the controller is adapted and configured to cause the insufflator to decrease or stop the flow of insufflation gas through the flow path when use of the suction device is stopped. In yet another aspect of the invention, the controller is adapted and configured to actuate a valve to control the amount of gas flowing through the flow path to compensate for the gas removed from the body cavity by the suction device. The controller is also adapted and configured to communicate with a recirculation pump for adjusting an amount of gas recirculating through the system, such as pressurized surgical gas circulating through a pneumatically sealed trocar.

In an embodiment of the invention, the suction device is also configured as an irrigation device, and a source of irrigation fluid is connected thereto. A fluid collection canister is also associated with the suction device. In another embodiment of the invention, a fluid pump is operatively associated with the source of irrigation fluid for delivering irrigation fluid to the irrigation device. In this instance, the fluid pump is operatively connected to and controlled by the controller.

In an embodiment of the invention, the vacuum source is a vacuum pump communicating with the suction device through the conduit, and a filter is operatively associated with the vacuum pump to filter exhaust gas from the vacuum pump. The vacuum pump is preferably operatively connected to and controlled by the controller. It is envisioned that a wired or wireless communication link can exist between the vacuum source and the controller.

The subject invention is also directed to a system for delivering insufflation gas to a body cavity of a patient, such as the patient's abdominal cavity, during an endoscopic procedures, such as a laparoscopic surgical procedure, which includes an insufflator for delivering a flow of insufflation gas to the abdominal cavity through a flow path that communicates with a pneumatically sealed trocar.

This system further includes a flow meter for measuring when the suction device is in use and an amount of gas that has been removed from the body cavity by use of a suction device, and a controller operatively connected to the flow meter for receiving a flow measurement from the flow meter to determine an amount of insufflation gas needed to be delivered to the body cavity by the insufflator to compensate for the gas removed from the body cavity by use of the suction device so as to maintain a stable pressure within the body cavity of the patient.

The subject invention is also directed to a system for delivering insufflation gas to an body cavity of a patient during an endoscopic surgical procedure, which includes an insufflator for delivering a flow of insufflation gas to the body cavity of the patient through a flow path that communicates with a pneumatically sealed trocar, a pump for circulating insufflation gas through the pneumatically sealed trocar to provide and maintain a gaseous seal therein, and a controller communicating with the insufflator and the pump. Here, the controller is configured to receive a signal from a surgical instrument used within the abdominal cavity and it is adapted to adjust the flow of new insufflation gas from the insufflator into the abdominal cavity and/or the circulation of existing insufflation gas by the pump.

In such an instance, the surgical device can be a suction device connected to a vacuum source for removing solid, liquids and gases from the abdominal cavity during the surgical procedure. Alternatively, the surgical device can be an electro-cautery device connected to an energy generator for cauterizing tissue during a surgical procedure. It is envisioned that the controller can communicate with the insufflator and the pump by a wired communication link or a wireless communication link.

These and other features of the multimodal gas delivery systems of the subject invention will become more readily apparent to those having ordinary skill in the art from the following enabling description of the preferred embodiments of the subject invention taken in conjunction with the several drawings described below.

BRIEF DESCRIPTION OF THE DRAWINGS

So that those having ordinary skill in the art will readily understand how to make and use the gas delivery systems and methods of the subject invention without undue experimentation, preferred embodiments thereof will be described in detail herein below with reference to the figures wherein.

DETAILED DESCRIPTION OF THE PREFERRED EMBODIMENTS

Figure 1:
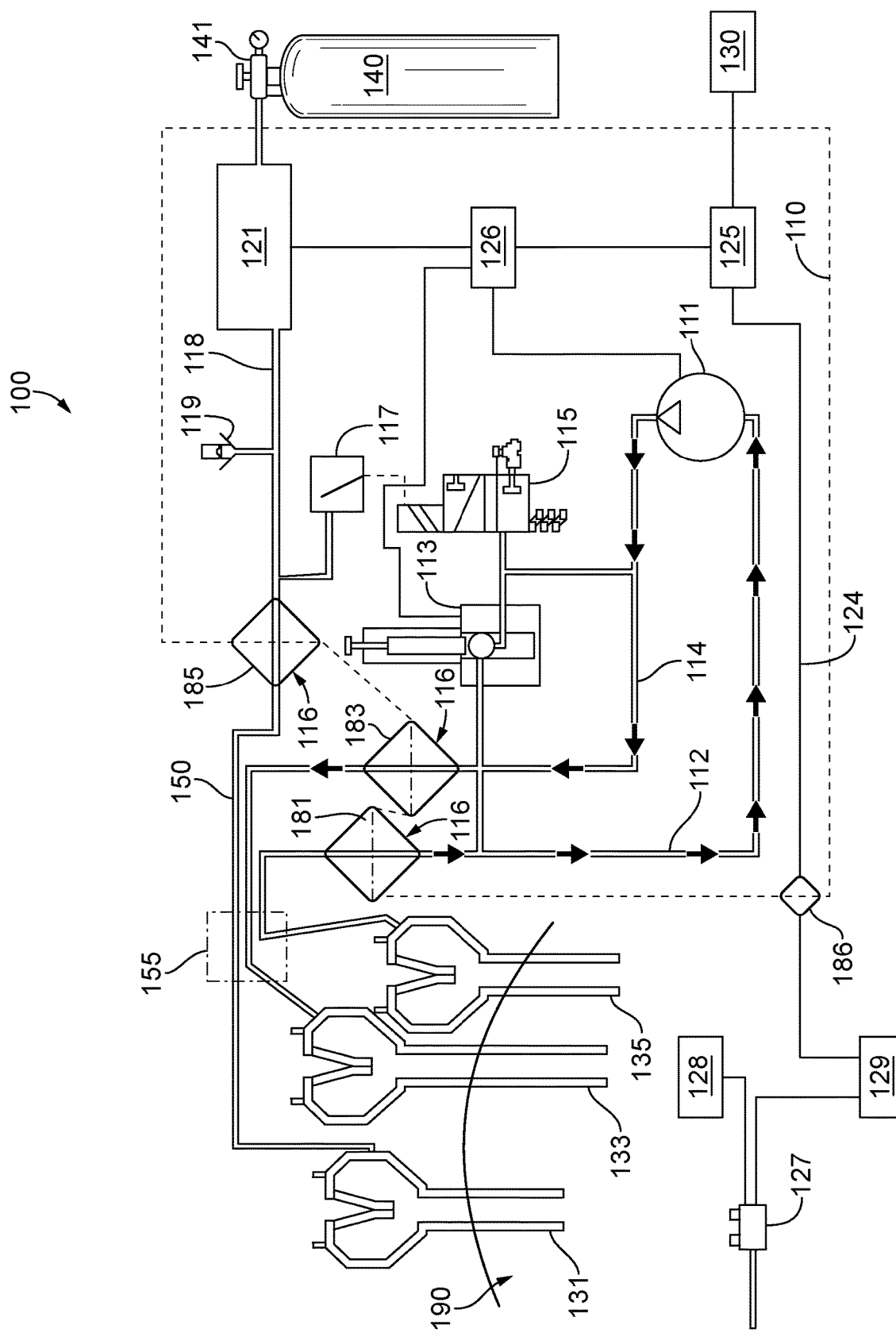
FIG. 1 is a schematic illustration of a multimodal surgical gas delivery system constructed in accordance with an embodiment of the subject invention and used with a suction device connected to a vacuum source and a flow meter for measuring when the suction device is in use and the amount of gas removed from the body cavity by the suction device.

Referring now to the drawings, wherein like reference numerals identify similar structural elements or features of the subject invention, there is illustrated in FIG. 1 a multimodal surgical gas delivery system constructed in accordance with a preferred embodiment of the subject invention and designated generally by reference numeral 100. As described in more detail below, the gas delivery system 100 is designed for multimodal operation to facilitate insufflation of a body cavity, smoke evacuation from the body cavity and/or gas recirculation through an access port communicating with the body cavity. In addition, the surgical gas delivery system 100 is configured to maintain body cavity pressure when suction is used within the body cavity during a surgical procedure to remove solid debris, liquids and gases from the body cavity.

As shown in FIG. 1, the gas delivery system 100 is adapted to function with three surgical access devices or trocars (131, 133, 135) that are in communication with a patient's body cavity 190. It is envisioned that gas delivery system 100 can also be used with two surgical access devices or trocars, as disclosed for example in commonly assigned U.S. Pat. No. 9,375,539. Alternatively, the system can be employed with a single surgical access device as disclosed for example in commonly assigned U.S. Pat. No. 9,295,490.

Figure 2:
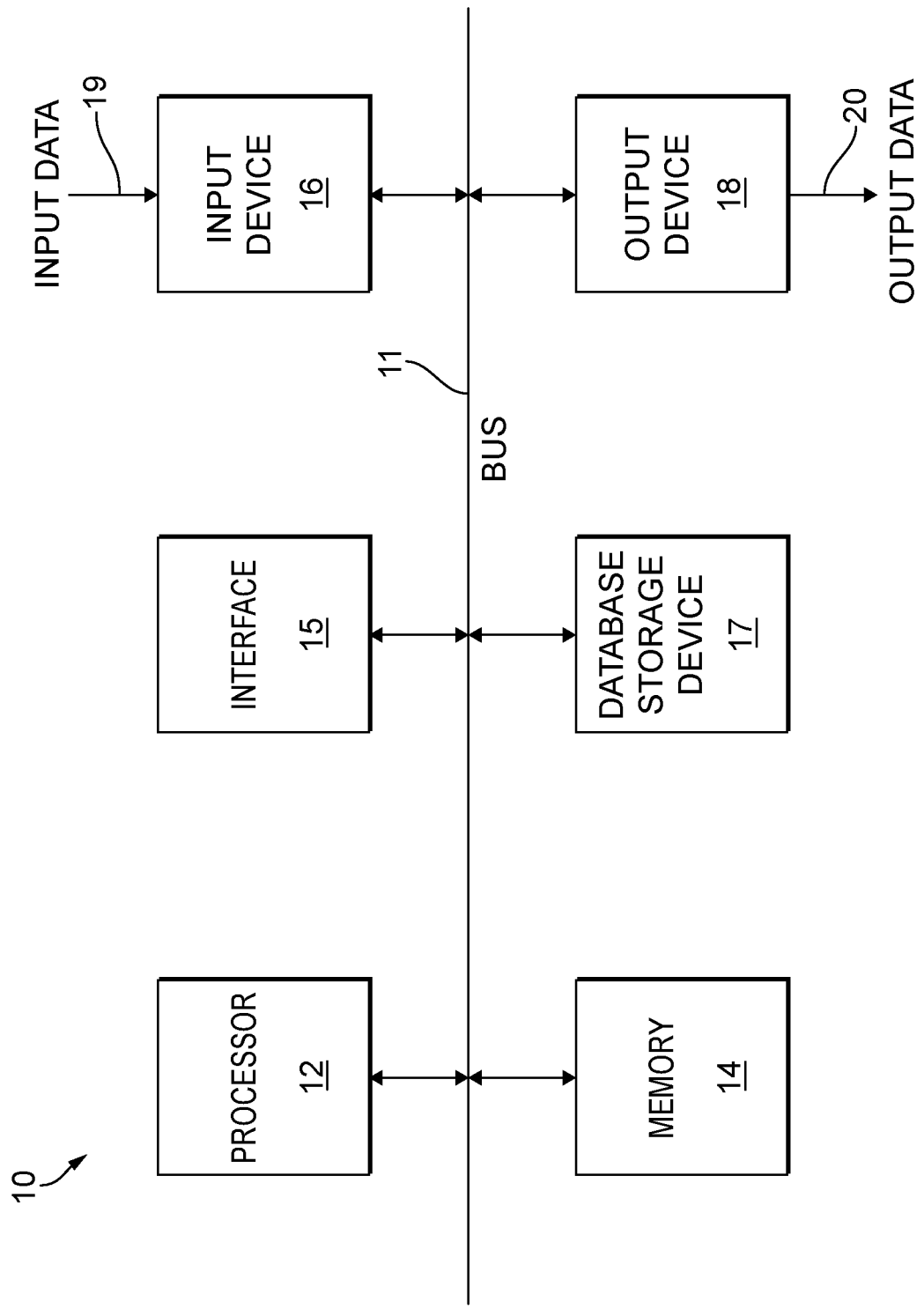
FIG. 2 is a schematic flow diagram of a computing environment that forms part of the multimodal surgical gas delivery system of FIG. 1.

The multimodal gas delivery system 100 includes a computer-controlled control unit 110 which is driven by a general purpose computing system that is best seen in FIG. 2. It is to be understood and appreciated that the computing system facilitates the selective modes of operation of multimodal gas delivery system 100.

Referring to FIG. 2, the computing system 10 of control unit 110 includes at least one processor 12, a memory 14, at least one input device 16 and at least one output device 18, which are all coupled together via a bus 11. The storage device 14 can be any form of data or information storage means, for example, volatile or non-volatile memory, solid state storage devices or magnetic devices.

In certain embodiments of the invention, input device 16 and output device 18 could be the same device. An interface 15 can also be provided for coupling the computing system 10 to one or more peripheral devices. For example interface 15 could be a PCI card or PC card. The memory or storage device 14 can house or maintain at least one database 17. The memory 14 can be any form of memory device, for example, volatile or non-volatile memory, solid state storage devices, or magnetic devices.

Input device 16 receives input data 19 and can comprise, for example, a keyboard, a pointer device such as a pen-like device, a mouse, a touch screen, or any other suitable device, such as a modem or wireless data adaptor, or data acquisition card. Input data 19 could come from different sources, for example keyboard instructions in conjunction with data received via a network.

Output device 18 produces or generates output data 20 and can comprise, for example, a display device or monitor in which case output data 20 is visual. Output data 20 could be distinct and derived from different output devices, for example a visual display on a monitor in conjunction with data transmitted to a network. A user could view data output, or an interpretation of the data output, on, for example, a monitor or using a printer.

In use, the computing system 10 is adapted to allow data or information to be stored in and/or retrieved from, via wired or wireless communication means, at least one database 17 stored in memory 14. The interface 15 may allow wired and/or wireless communication between the processing unit 12 and peripheral components that may serve a specialized purpose.

Preferably, the processor 12 receives instructions as input data 19 via input device 16 and can display processed results or other output to a user by utilizing output device 18. More than one input device 16 and/or output device 18 can be provided. It should be appreciated that the computing system 10 may be in any form, but it is preferably provided integral with the control unit 110 of surgical gas delivery system 100.

It is to be appreciated that the computing system 10 may be a part of a networked communications system. Computing system 10 could connect to a network, for example the Internet or a WAN. Input data 19 and output data 20 could be communicated to other devices via the network. The transfer of information or data over the network can be achieved using wired communications means or wireless communications means. A server can facilitate the transfer of data between the network and one or more databases. A server and one or more databases provide an example of an information source.

Thus, the computing system 10 may operate in a networked environment using logical connections to one or more remote computers. The remote computer may be a personal computer, a server, a router, a network PC, a tablet device, a peer device, or other common network node, and typically includes many or all of the elements described above.

Referring once again to FIG. 1, the multimodal surgical gas delivery system 100 includes a fluid pump 111 that is adapted and configured to circulate pressurized insufflation fluid through the system 100. A supply conduit 114 is in fluid communication with an output of the fluid pump 111 and it is configured and adapted for delivering pressurized insufflation fluid to an output port 183 of the control unit 110.

A return conduit 112 is in fluid communication with an input of the fluid pump 111 for delivering insufflation fluid to the fluid pump 111, and it is configured and adapted for returning insufflation fluid to an input port 181 of the control unit 110. An adjustable back-pressure control valve 113 is provided in fluid communication with the supply conduit 114 and the return conduit 112, and is adapted and configured to respond to a supply conduit pressure exceeding a set pressure, by opening and directing fluid from the supply conduit 114 to the return conduit 112. The back-pressure control valve 113 can be a mechanical valve, such as a resiliently-biased valve. Alternatively, the back-pressure control valve 113 can be an electro-mechanical valve, responding to a high pressure signal from one or more pressure sensors (e.g. 117) within the system 100.

An insufflation subunit 121 is provided and it is adapted and configured to receive a supply of insufflation gas (e.g., carbon dioxide) from a source 140 such as a local tank as shown or from a central distribution system, which may also pass through a pressure regulator 141 prior to entering the gas delivery system 100. The insufflation subunit 121 delivers insufflation gas to the rest of the system 100 through an insufflation conduit 118. The insufflation subunit 121 includes an internal pressure sensor (not shown) that senses the pressure of surgical cavity 190 through the insufflation conduit 118, and an insufflation control (not shown) periodically stops and starts the addition of insufflation fluid into the system 100 from the source 140 to facilitate periodic pressure measurements.

The gas delivery system 100 is operated or otherwise controlled by a user through a control panel, such as one provided on or otherwise in connection with the control unit 110. Such a control panel is preferably adapted and configured to permit a user to select a mode for the multimodal surgical gas delivery system, such as by way of a switch, touch screen or other user interface. For example a graphical user interface (GUI) can be provided that permits the selection of an operating mode as well as the operational parameters for a particular mode. It is to be understood and appreciated that the control panel may be provided integral with the system 100 or it can be remotely located therefrom using known means of data communication.

Operating modes can include, but are not limited to, insufflation, smoke evacuation, combined smoke evacuation and insufflation, recirculation, or combined recirculation and smoke evacuation. Operating parameters for a mode can include, for example, flow rate (e.g., liters/minute), pressure (e.g., mmHg), and conditioning parameters (e.g., temperature and humidity), and the like.

As used herein, the "recirculation" mode, alone or combined with other modes, is one that is suitable for providing sufficient operating pressures and flow rates to drive pneumatically sealed surgical access devices such as those described in commonly assigned U.S. Pat. Nos. 7,854,724 and 8,795,223, incorporated herein by reference.

A tube set 150 is also provided and it is adapted and configured to connect at one end to the supply conduit 114, return conduit 112 and insufflation conduit 118, and at the opposing end to a plurality of surgical access devices 131, 133, 135, which are in fluid communication with the surgical cavity 190. The configuration of the tube set 150 can vary, depending on the desired implementation, as mentioned above. In the case of the system 100, the tube set 150 preferably has a unitary, multi-lumen connection to input 181, output 183 and insufflation 185 ports, and separate connections to the individual surgical devices 131, 133, 135. It is envisioned that the tube set 150 can have a compound, multi-lumen tube, beginning at the connections to the ports 181, 183, 185 for a predetermined distance from the control unit 110, and at an intermediate point a furcation 155 yields multiple separate tubes. In the case of the system 100, three separate tubes, separately lead to each of the surgical devices 131, 133, 135, which may be surgical access devices with insufflation capability, or other instruments, such one or more veress needles. The surgical devices 131, 133, 135 are thus individually connected to one of the supply conduit 114, return conduit 112 and insufflation conduit 118, and therefore respectively facilitate that function.

As set forth above, in one preferred aspect, the separate distal tube portions of the tube set 150 are connected by way of a conventional fitting, such as a luer-lock fitting on a conventional surgical device. The precise configuration of the tube set 150 can vary depending on the desired configuration. An example of a fitting for a multi-lumen tube set is described in commonly assigned U.S. Pat. No. 9,526,886, the disclosure of which is herein incorporated by reference in its entirety.

A disposable filter 116 is also associated with the tube set 150, either separate therefrom or integral therewith. A filter suitable for use with a multimodal gas delivery system 100 with insufflation, smoke evacuation and recirculation functionality for use with specialized pneumatically sealed surgical access devices is disclosed in U.S. Pat. Nos. 9,067,030 and 9,526,849, the disclosures of which are herein incorporated by reference in their entireties.

It is envisioned that the disposable tube sets 150 and/or filters 116 used in connection with the system 100, can be provided with identification devices that permit authorized use or otherwise prevent unauthorized use. Such identification devices can include, but are not limited to, a radio-frequency identification (RFID) transponder, computer readable data chip, bar code or other data-carrying element provided thereon. It is also envisioned that the identification device on the filter or tube set could cause or otherwise instruct the gas delivery system 100 to automatically switch into or launch in a particular operating mode (e.g., recirculation, smoke evacuation, or standard insufflation).

With continuing reference to FIG. 1, system 100 further includes a second dump valve 115 in connection with the fluid supply conduit 114. In addition, to the short-circuiting action of the back-pressure control valve 113 described above, the system 100 is provided with a pressure sensor 117, which can be mechanical or electronic as illustrated. Sensor 117 is in fluid communication with the insufflation conduit 118 or other source of abdominal pressure. When an over-pressure condition is sensed, the pressure sensor 117 signals the dump valve 115 to release fluid out of the system 100.

System 100 can be employed with one surgical device 131 being used for insufflation and sensing functions, and another surgical device 135 serving to remove insufflation gas from the abdomen, which then passes through a filter, such as an ultralow-penetration air ("ULPA") filter element 116 for example, before returning to the pump 111. The filter 116 is preferably configured and adapted to clear all or essentially all smoke and debris from the gas passing therethrough, with the gas being returned to the abdominal cavity 190 through a third surgical device 133. As illustrated, another filter element 116 can be provided in connection with the supply conduit 114 leading from the pump 111.

With continuing reference to FIG. 1, as noted above, the gas delivery system 100 of the subject invention is configured to maintain body cavity pressure when suction is used in the body cavity during a surgical procedure. In this regard, the insufflator control unit 110 further includes a conduit 124 that facilitates fluid communication between suction device 127 and vacuum source 130. A flow meter 125 communicates with the conduit 124 for measuring the amount of gas flowing through conduit 124. The flow meter 125 sends a measurement signal to the controller 126 indicating the amount of gas flow. Controller 126 uses the measurement signal that is provided by the flow meter 125 to determine the amount of insufflation gas needed to compensate for the amount of gas that is removed from surgical cavity 190 by the suction device 127.

Controller 126 accomplishes gas removal compensation in one of several ways. For example, controller 126 can communicate with the insufflation subunit 121 to increase the insufflation gas flow through conduit 118. Alternatively, controller 126 can actuate a valve, for example, valve 113, to increase insufflation gas output or reduce the amount of gas being recirculated through the system. In another embodiment, the controller 126 can communicate with a pump, for example, fluid pump 111 to adjust the insufflation gas flow through the system. Regardless of the action taken to compensate for the gas removed from the body cavity 190 by the suction mechanism 127, the stability of the pneumoperitoneum within the body cavity 190 is maintained in any selected operational mode.

The suction mechanism 127 is preferably a combined suction/irrigation instrument, such as the devices disclosed for example in U.S. Pat. No. 5,609,573, 6,527,743, or 6,918,902, the disclosures of which are incorporated herein by reference in their entireties. These instruments are typically designed to allow a user to activate suction or irrigation by pressing a button or pulling a trigger on the instrument itself. The irrigation portion of the suction/irrigation instrument 127 is connected to a liquid source 128, for example, an IV bag of saline solution. The suction portion of suction/irrigation instrument 127 is connected to a fluid collection canister 129, which is in turn connected via input port 186 to control unit 110 through conduit 124. Conduit 124 connects to a vacuum source 130, for example, a conventional wall vacuum source or a conventional stand-alone vacuum source.

Figure 3:
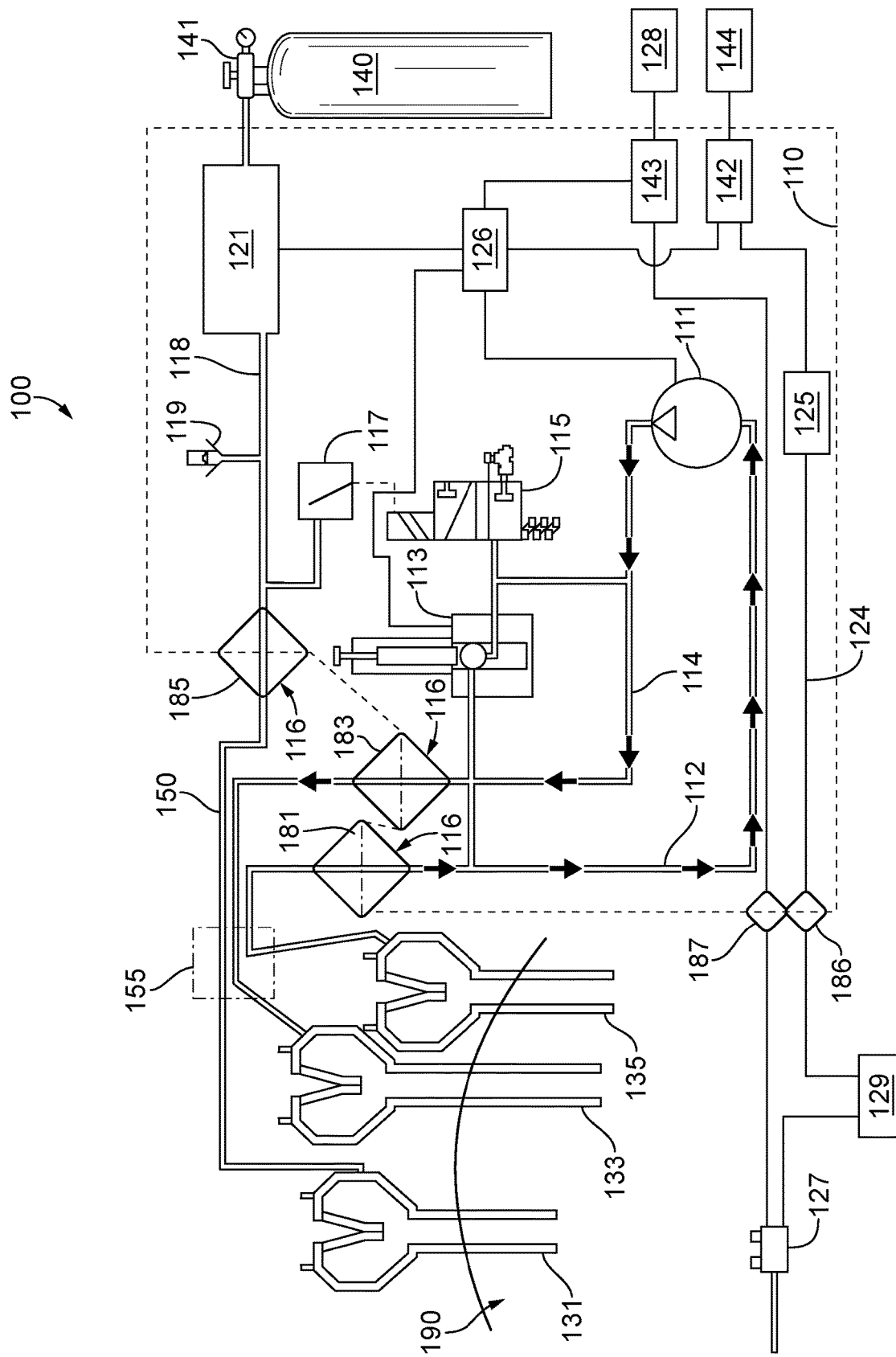
FIG. 3 is a schematic illustration a multimodal surgical gas delivery system as in FIG. 1, which is used with a suction device connected to a pump and a flow meter for measuring the amount of gas removed from the body cavity by the suction device.

Referring to FIG. 3, in another embodiment of the gas delivery system 100 of the subject invention, the vacuum source for suction can be physically located or otherwise included with the control unit 110. In this instance, pump 142 causes gas to be pulled from the suction portion of suction/irrigation instrument 127 through conduit 124. The system 100 then operates to maintain stability of the pneumoperitoneum at the surgical cavity 190 by way of the flow meter 125, as described above with reference to FIG. 1.

A filter 144 is provided to filter exhaust gas from pump 142 and it can be positioned anywhere downstream from the fluid collection canister 129. As shown, the control unit of gas delivery system 100 further includes a fluid pump 143 that is used to pump fluid from the liquid source 128 through conduit 145 to the irrigation portion of suction/irrigation instrument 127. The irrigation portion of suction/irrigation instrument 127 is connected with control unit 110 through output port 187.

Actuation of pumps 142 and 143 can be controlled by controller 126 upon receiving a signal from suction/irrigation instrument 127. Alternatively, pumps 142 and 143 can remain in an operational state when the system 100 is operational with suction and irrigation functionality being controlled by the suction/irrigation instrument 127. Alternative embodiments of system 100 can include either or both of pumps 142 and 143. This embodiment is compatible with each of the first, second, and third modes of operation described above. It is also contemplated that pump 142 or pump 143 or both can be operated independently of system 100 so as to effect suction, irrigation, or both independently without affecting the supply of insufflation gas. An example of this type of operating mode is the use of suction/irrigation in a non-laparoscopic procedure where insufflation is not necessary.

An additional advantage of the system 100 of the subject invention provided by connecting the suction mechanism 127 directly or indirectly to the insufflation subunit 121 by way of the controller 126 is that the system is able to stop insufflation, in real time, when the use of the suction device 127 is stopped. That is, when the surgeon is no longer activating the suction mechanism 127, insufflation gas flow will immediately return to a normal condition. This ability to immediately stop insufflating when suction stops, prevents overpressure conditions and pressure spikes in the body cavity. This capability is in contrast to conventional insufflators that will typically increase insufflation to maintain cavity pressure as suction is applied, and when suction is stopped, the insufflator will typically continue to operate, which can cause a pressure spike within the body cavity.

By way of example, referring to FIG. 1, during a surgical procedure, when the suction mechanism 127 is activated to clear debris, smoke or fluids from the body cavity, the flow meter may measure 30 L/min of flow through conduit 124, causing the controller to command the insufflation unit 121 to increase the flow of insulation gas to the body cavity through conduit 118. When suction is stopped, there will no longer be flow through conduit 124, so the flow meter 125 will measure 0 L/min of flow and can command the insufflation unit 121 to stop, decrease or otherwise return to a normal or otherwise predetermined rate of gas flow in real time.

Alternatively, in the configuration of FIG. 3, when the vacuum pump 130 is activated, a signal is sent to the controller through link 146 so that the controller 126 can command the insufflation subunit 121 to increase gas flow, and when the vacuum pump 130 is stopped, a corresponding signal is sent to the controller 126 through link 146 so that the controller 126 can responsively command the insufflation subunit 121 to return to normal flow conditions.

Figure 4:
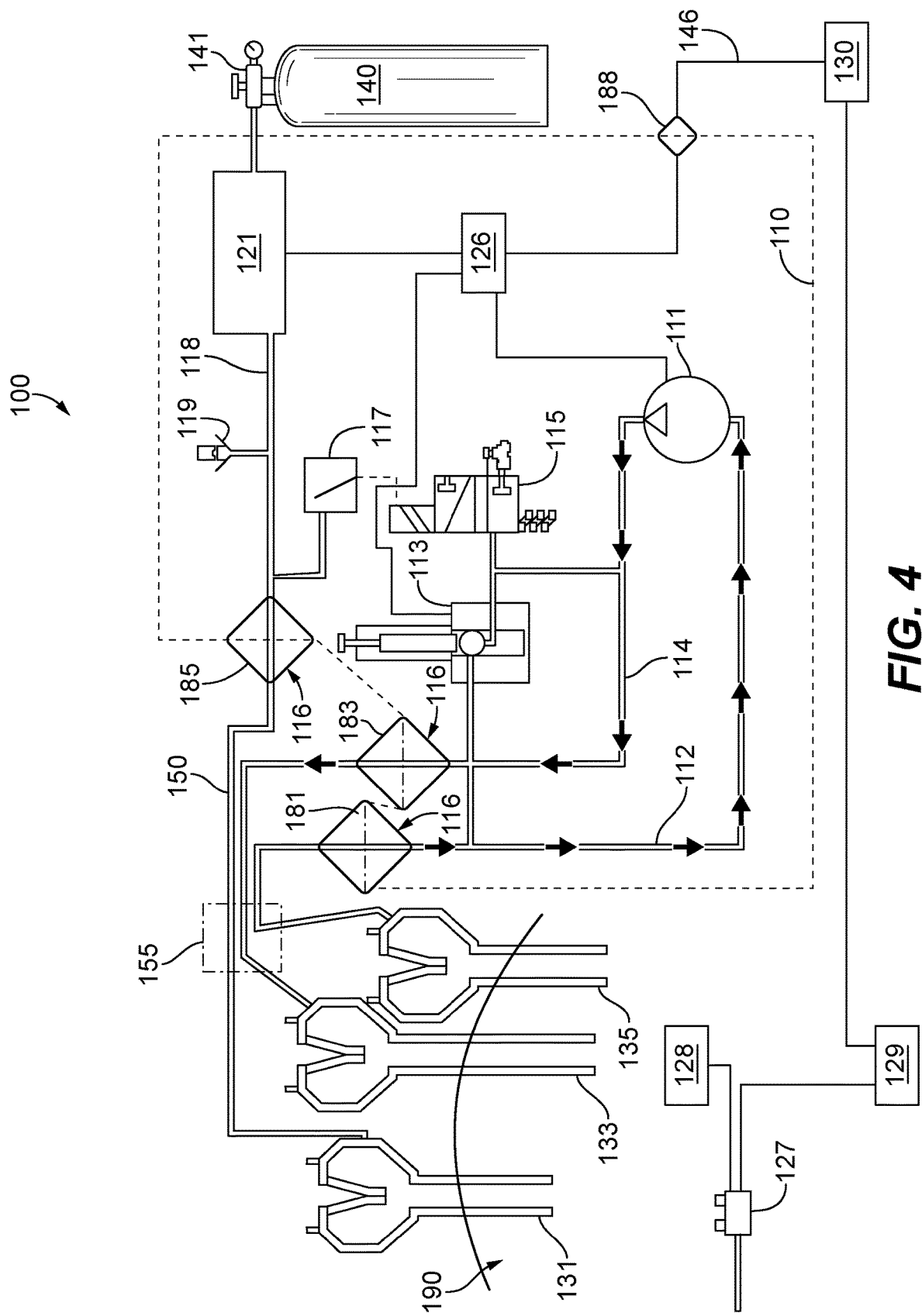
FIG. 4 is a schematic illustration of a multimodal surgical gas delivery system as in FIG. 1, which is used with a suction device connected to a vacuum source, which communicate with a controller through a wired or wireless communication link.

Referring to FIG. 4, in another embodiment the control unit 110 of gas delivery system 100 is configured to receive a signal from the suction/irrigation system 127 indicating that suction at the surgical cavity 190 has been initiated. As shown, the signal is received via a wired connection 146 between control unit 110 and the suction/irrigation system through a communication port 188.

Alternatively, this communication can occur wirelessly, for example, through a Bluetooth or near-field communication (NFC) connection. Bluetooth and near field communication share several features, both being forms of wireless communication between devices over short distances. NFC is limited to a distance of approximately four centimeters while Bluetooth can reach over thirty feet.

In the embodiment of FIG. 4, the gas delivery system 100 includes suction/irrigation instrument 127, a liquid source 128, fluid collection canister 129 and a vacuum source 130. Controller 126 uses the signal provided by communication port 188 to adjust the amount of insufflation gas needed to compensate for the gas removed from surgical cavity 190 by the suction/irrigation system. When the signal from the suction/irrigation system includes information on suction flow, the control unit 110 compensates for insufflation gas flow as described above. Alternatively, control unit 110 can respond in a predetermined manner, for example, by increasing insufflation gas flow by a predetermined amount.

It is envisioned that other surgical instruments can communicate with the control unit 110 of gas delivery system 100 using this communication system. For example, many surgical procedures involve the use of an electro-cautery instrument to cut or coagulate tissue. Typically, smoke is generated within the surgical cavity 190 when these instruments are used. It can be desirable to remove the smoke from the surgical cavity during the surgical procedure to improve visualization at the cavity. Often this is done by way of suction, which adversely can affect the stability of the pneumoperitoneum of the surgical cavity 190.

Other methods of smoke removal require introducing large amounts of new insufflation gas or maintaining high amounts of insufflation gas recirculation. It would be advantageous to target smoke evacuation to those times when smoke is being generated to lower the amount of insufflation gas being provided to surgical cavity 190 or maintain the stability of the pneumoperitoneum at the surgical cavity 190.

Figure 5:
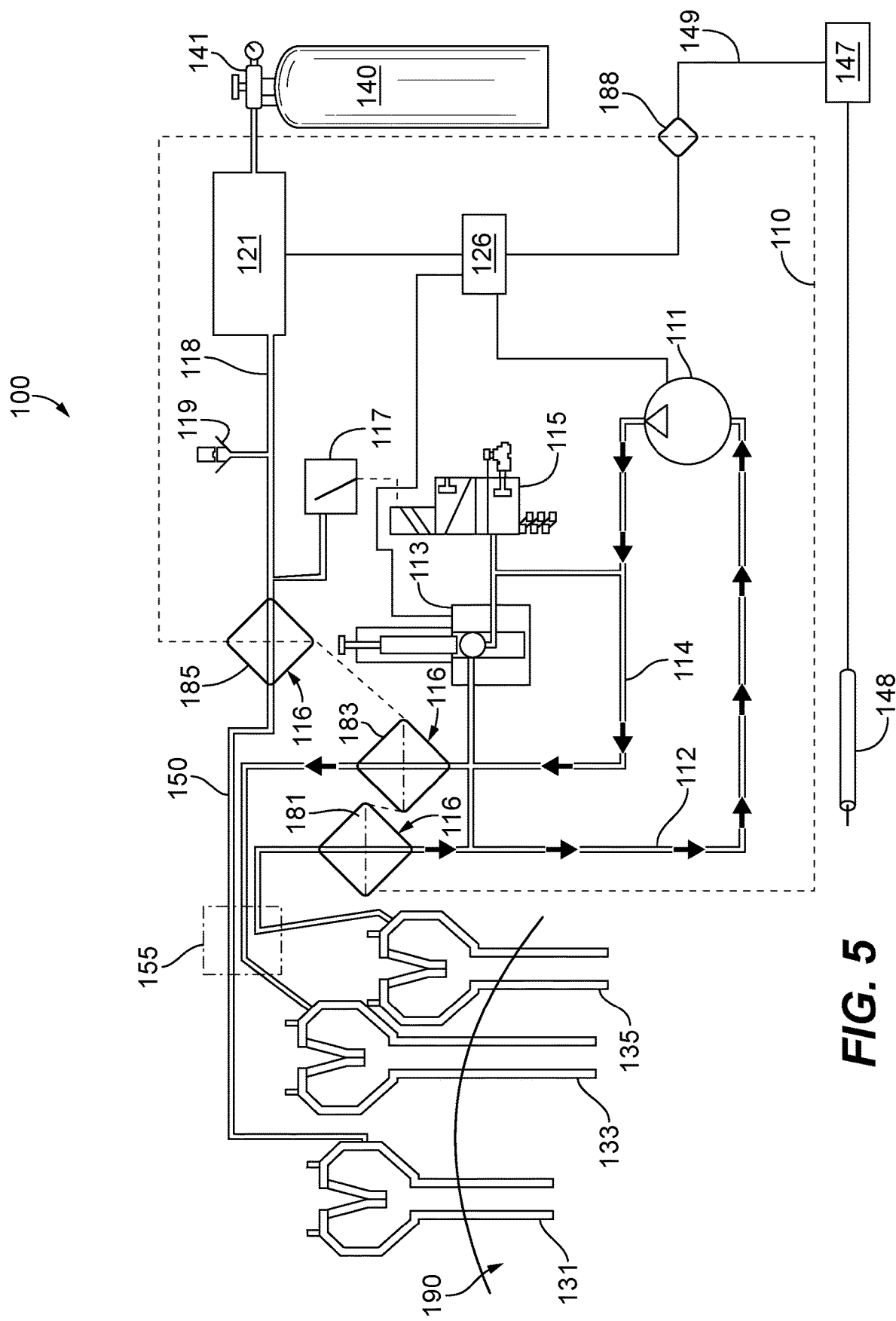
FIG. 5 is a schematic illustration of a multimodal surgical gas delivery system as in FIG. 1, which is used with an electro-cautery device connected to an energy generator, which communicate with a controller through a wired or wireless communication link.

Referring to FIG. 5, there is illustrated the gas delivery system 100 of the subject invention wherein the control unit 110 is operatively associated with an electro-cautery system including an electro-cautery device 148 and an energy generator 147. Suitable examples of an electro-cautery energy generators that can be employed in this manner are disclosed in U.S. Pat. Nos. 7,972,329, 7,736,358, and 7,540,871, the disclosures of which are incorporated herein by reference in their entireties.

The control unit 110 receives a signal from the electro-cautery device 148 and/or the energy generator 147 indicating that electro-cautery instrument 148 is being used in the surgical cavity 190. The signal is received via a wired connection 149 between control unit 110 and the electro-cautery system through a communication port 188. Alternatively, this communication can occur wirelessly, for example, through a Bluetooth or near-field connection. The controller 126 uses the signal provided to communication port 188 to adjust the flow of new insufflation gas from the insufflation unit 121 or the recirculation of existing insufflation gas by the pump 111 to facilitate improved smoke removal form surgical cavity 190.

In use, after receiving a signal from the electro-cautery system indicating that electro-cautery instrument 148 is not being used at surgical cavity 190, the controller 126 can readjust the flow of new insufflation gas to the body cavity or the recirculation of existing insufflation gas to an adequate level. It is also contemplated that the electro-cautery system and the control unit 110 can be combined in the same unit and used independently of each other or in conjunction with each other.

While the subject disclosure has been shown and described with reference to preferred embodiments, those skilled in the art will readily appreciate that changes and/or modifications may be made thereto without departing from the scope of the subject disclosure.

What is claimed is:

1. A system for delivering insufflation gas to a body cavity of a patient during a surgical procedure, comprising:
    a) an insufflator for receiving a supply of insufflation gas from a gas source by way of a pressure regulator and for delivering insufflation gas to the body cavity of the patient at a predetermined flow rate through a flow path that communicates with a first trocar, and wherein a control valve and a recirculation pump are provided to establish a stable pneumoperitoneum in the body cavity, wherein a supply conduit communicates with an output of the recirculation pump for delivering pressurized gas to the body cavity by way of a second trocar and a return conduit communicates with an input of the recirculation pump for returning gas to the recirculation pump from the body cavity by way of a third trocar;
    b) a suction device connected to a vacuum pump for removing solids, liquids and gases from the body cavity during the surgical procedure, wherein gas is removed from the body cavity by the suction device at a higher flow rate than the predetermined flow rate at which insufflation gas is delivered to the body cavity by the insufflator, causing the pneumoperitoneum in the body cavity to become unstable;
    c) a suction conduit outside of the flow path, the supply conduit and the return conduit, providing communication between the vacuum pump and the suction device;
    d) a flow meter communicating with the suction conduit for measuring an amount of gas flowing through the suction conduit that has been removed from the body cavity by use of the suction device; and
    e) a controller operatively connected to the flow meter for receiving a flow measurement from the flow meter to determine when the suction device is in use and an amount of insufflation gas needed to be delivered to the body cavity by the insufflator through the first trocar to compensate for the amount of gas that has been removed from the body cavity by use of the suction device,
    wherein the controller is adapted and configured to communicate with the insufflator, the control valve and the recirculation pump to adjust an amount of gas circulating through the system by way of the second and third trocars so as to maintain the stability of the pneumoperitoneum within the body cavity when the suction device is used during the surgical procedure, and
    wherein the suction device is operatively connected to the insufflator by way of the controller so that when use of the suction device is stopped, the controller causes the insufflator to immediately return to delivering insufflation gas to the body cavity through the first trocar at the predetermined flow rate to prevent overpressure conditions and pressure spikes in the body cavity.

2. The system of claim 1, wherein the controller is adapted and configured to cause the insufflator to increase the amount of insufflation gas needed through the flow path to compensate for the amount of gas that has been removed from the body cavity by the suction device.

3. The system of claim 1, wherein the controller is adapted and configured to cause the insufflator to decrease or stop the amount of insufflation gas needed through the flow path when use of the suction device is stopped.

4. The system of claim 1, wherein the controller is adapted and configured to actuate the control valve to control the amount of gas flowing through the flow path to compensate for the amount of insufflation gas that has been removed from the body cavity by the suction device by increasing insufflation gas output or reducing the amount of gas recirculating through the system.

5. The system of claim 1, wherein the suction device is also configured as an irrigation device, and wherein a source of irrigation fluid is connected thereto.

6. The system of claim 5, wherein a fluid collection canister is associated with the suction device.

7. The system of claim 5, wherein a fluid pump is operatively associated with the source of irrigation fluid for delivering irrigation fluid to the irrigation device.

8. The system of claim 7, wherein the fluid pump is operatively connected to and controlled by the controller.

9. The system of claim 1, wherein a filter is operatively associated with the vacuum pump to filter exhaust gas from the vacuum pump.

10. The system of claim 1, wherein a wired communication link exists between the vacuum pump and the controller.

11. The system of claim 1, wherein a wireless communication link exists between the vacuum pump and the controller.

* * * * *